(12) United States Patent
Safai

(10) Patent No.: US 9,511,393 B2
(45) Date of Patent: Dec. 6, 2016

(54) FLEXIBLE ULTRASOUND INSPECTION SYSTEM

(75) Inventor: Morteza Safai, Newcastle, WA (US)

(73) Assignee: THE BOEING COMPANY, Chicago, IL (US)

( * ) Notice: Subject to any disclaimer, the term of this patent is extended or adjusted under 35 U.S.C. 154(b) by 479 days.

(21) Appl. No.: 13/588,437

(22) Filed: Aug. 17, 2012

(65) Prior Publication Data

US 2014/0047924 A1    Feb. 20, 2014

(51) Int. Cl.
| | |
|---|---|
| *G01N 29/04* | (2006.01) |
| *B06B 1/02* | (2006.01) |
| *B06B 1/06* | (2006.01) |
| *G01N 29/28* | (2006.01) |
| *G01N 29/34* | (2006.01) |

(52) U.S. Cl.
CPC .......... *B06B 1/0207* (2013.01); *B06B 1/0622* (2013.01); *G01N 29/28* (2013.01); *G01N 29/34* (2013.01); *B06B 2201/76* (2013.01); *G01N 2291/106* (2013.01); *G01N 2291/2694* (2013.01); *Y10T 29/42* (2015.01)

(58) Field of Classification Search
CPC ..................................................... H01L 41/22
USPC .................................. 73/644, 587; 29/25.35
See application file for complete search history.

(56) References Cited

U.S. PATENT DOCUMENTS

| | | | | |
|---|---|---|---|---|
| 5,915,277 A | * | 6/1999 | Patton .............................. | 73/601 |
| 6,899,682 B2 | * | 5/2005 | Eberle .................. | A61B 1/0011 600/459 |
| 7,567,649 B1 | * | 7/2009 | Safai ......................... | G01T 1/24 250/370.09 |
| 8,151,643 B2 | * | 4/2012 | De Smet ................ | G01H 11/08 73/587 |
| 8,193,685 B2 | * | 6/2012 | Klee ..................... | B06B 1/0292 310/313 R |
| 2004/0118599 A1 | * | 6/2004 | Chason et al. ................. | 174/260 |
| 2004/0215409 A1 | * | 10/2004 | Adewole ........... | G06K 19/0717 702/81 |
| 2008/0100587 A1 | * | 5/2008 | Sano ....................... | G06F 3/041 345/173 |
| 2008/0135947 A1 | * | 6/2008 | Koo et al. ..................... | 257/392 |
| 2010/0280388 A1 | | 11/2010 | Huang | |
| 2012/0065930 A1 | * | 3/2012 | Allee et al. ................... | 702/150 |

(Continued)

FOREIGN PATENT DOCUMENTS

WO    WO 2011127331 A2 * 10/2011 ............... G01V 9/00

OTHER PUBLICATIONS

Journal of Applied Physics 97, 093708 (2005) Mechanical force sensors using organic thin-film transistors.*

(Continued)

*Primary Examiner* — Michael A Lyons
*Assistant Examiner* — Suman K Nath
(74) *Attorney, Agent, or Firm* — Yee & Associates, P.C.

(57) ABSTRACT

A method and apparatus comprising an array of piezoelectric elements, a flexible substrate connected to the array of piezoelectric elements, and an organic circuit system formed on the flexible substrate and connected to the array of piezoelectric elements. The flexible substrate is configured to substantially conform to a surface of a test object. The organic circuit system is configured to cause the array of piezoelectric elements to send sound signals into the test object.

18 Claims, 7 Drawing Sheets

(56) References Cited

U.S. PATENT DOCUMENTS

2012/0119622 A1* 5/2012 Matthews .............. G01B 17/02
310/336
2013/0192356 A1* 8/2013 De Graff et al. .......... 73/152.01

OTHER PUBLICATIONS

Darlinski et al., "Mechanical force sensors using organic thin-film transistors," Journal of Applied Physics, vol. 97, Apr. 2005, pp. 93708-1-93708-4.
Firester, "Macroelectronics: large area flexible electronics for sensors, displays, and other applications," Proceedings of SPIE, Defense, Security, and Cockpit Displays, vol. 5443, Dec. 2004, pp. 29-37.
PCT search report dated Jul. 18, 2013 regarding application PCT/US2013/037208, filed Apr. 18, 2013 reference 12-0505-PCT, applicant The Boeing Company, 11 pages.
Po-Yuan et al., "Flexible Glass Substrates for Organic TFT Active Matrix Electrophoretic Displays," Industrial Technology Research Institute, May 2011, 15 Pages.
Anthony et al., "Organic Electronics," Organic Electronics Group at Wake Forest, Sep. 2010, 4 Pages, accessed Jul. 24, 2012 http://www.wfu.edu/~jurcheod/research/.
Sankir, "Flexible Electronics: Materials and Device Fabrication," Dissertation, Virginia Polytechnic Institute and State University, Dec. 2005, 172 Pages.
International Preliminary Report on Patentabilty, dated Feb. 17, 2015, regarding Application No. PCT/US2013/037208, 7 pages.

\* cited by examiner

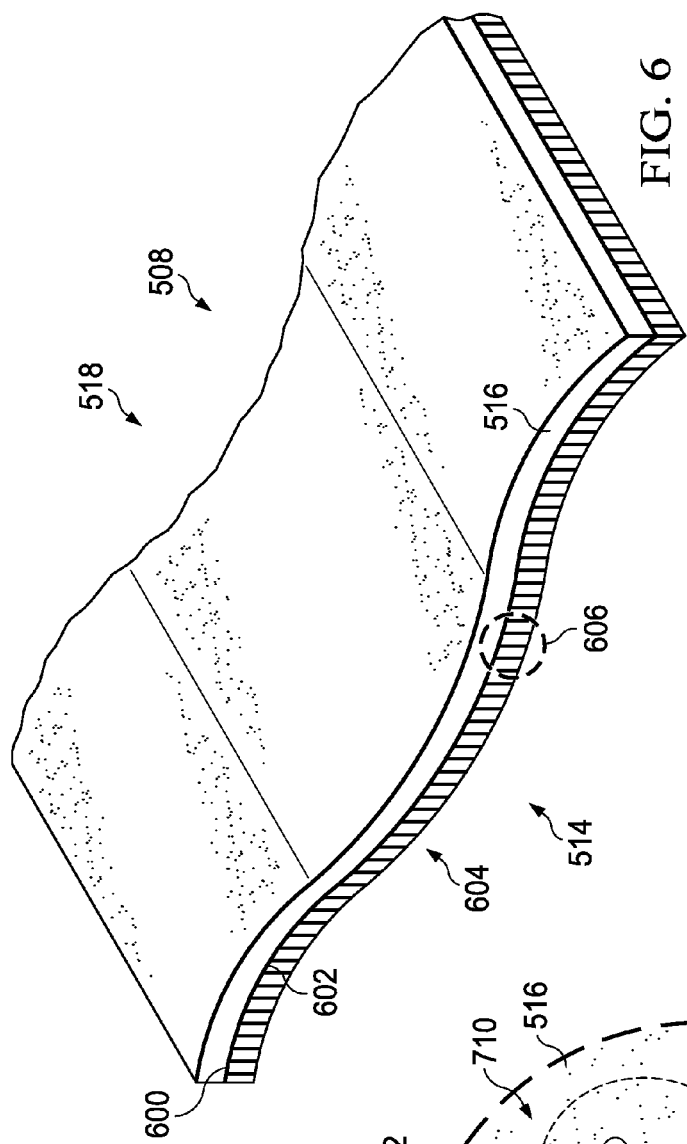
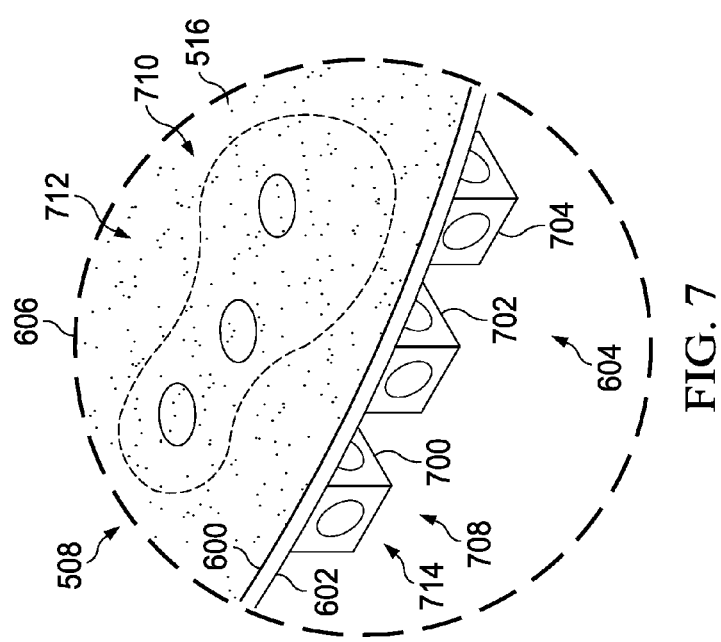

FLEXIBLE ULTRASOUND INSPECTION SYSTEM

BACKGROUND INFORMATION

1. Field

The present disclosure relates generally to inspecting objects and, in particular, to the nondestructive inspection of objects. Still more particularly, the present disclosure relates to a method and apparatus for performing nondestructive inspections of an object using a flexible ultrasound inspection system.

2. Background

Nondestructive inspection involves evaluating an object without causing damage to the object. This type of inspection may include evaluating properties of the object without causing permanent changes. These inspections may be used to identify undesirable and desirable properties.

For example, nondestructive inspection may be used to identify inconsistencies in composite parts. These inconsistencies may include, for example, voids, delaminations, disbonding, and other features that may cause the composite part to perform at a level that is less than desired.

Nondestructive inspection techniques may include, for example, ultrasound testing, remote visual inspection, eddy current testing, x-ray testing, and other suitable types of techniques. With ultrasound testing, an ultrasound transducer is typically coupled to a test object. The coupling may be performed using a couplet such as oil, water, or other types of couplets.

The ultrasound transducer is configured to send sound signals into the test object. Response sound signals are detected by the same transducer or a different transducer. The response sound signals may be reflections of some of the sound signals sent by the transducer and may come from an interface such as the back wall of a test object or an inconsistency in the test object. The response sound signals may be displayed or otherwise analyzed to determine whether undesired inconsistencies are present in the test object.

An ultrasound inspection system with a single transducer may be used to inspect the entire surface of the test object. With a single transducer, that transducer is moved over the surface of the test object that is being inspected. This process, however, may take more time than desired.

When testing objects with large surface areas, transducer arrays with multiple transducers may be used to provide greater coverage as compared to using a single transducer. With an array of transducers, the array itself is moved and sound signals may be sent into the test object in a larger area as compared to a single transducer. In this manner, a transducer array may be used to perform an inspection of an object more quickly than a single transducer is able to perform the same inspection.

Although using transducer arrays may reduce the amount of time needed to inspect test objects, when non-planar surfaces are present, the ability of a transducer array to generate desired response sound signals may be reduced. For example, transducer arrays are typically connected to a rigid frame. If a surface is non-planar, some of the transducers in the transducer array may not have a desired coupling to the surface of the object. If the transducers in the transducer array are not coupled to the surface properly, the response sound signals may not accurately reflect properties in the test object.

In some cases, the transducer array frame may have segments that are moveable relative to each other. Transducers on the different segments may then be repositioned to more closely conform to the shape of the surface of the test object.

Even with these positionable segments, the transducers ability to conform to curves of some test objects may be infeasible. As a result, the use of a smaller sized transducer array or a single transducer may then be used to test these sections of the test object with curved surfaces that are too great for the array. This type of inspection, however, may take more time and effort than desired. Therefore, it would be desirable to have a method and apparatus that takes into account at least some of the issues discussed above, as well as other possible issues.

SUMMARY

In one illustrative embodiment, an apparatus comprises an array of piezoelectric elements, a flexible substrate connected to the array of piezoelectric elements, and an organic circuit system formed on the flexible substrate and connected to the array of piezoelectric elements. The flexible substrate is configured to substantially conform to a surface of a test object. The organic circuit system is configured to cause the array of piezoelectric elements to send sound signals into the test object.

In another illustrative embodiment, a method for inspecting a test object is present. A flexible ultrasound device is positioned on a surface of the test object. The flexible ultrasound device includes an array of piezoelectric elements, a flexible substrate connected to the array of piezoelectric elements and configured to substantially conform to the surface of the test object, and an organic circuit system formed on the flexible substrate and connected to the array of piezoelectric elements. Sound signals are sent into the test object from the array of piezoelectric elements. Response sound signals are detected in the test object at the array of piezoelectric elements. The response sound signals are generated in response to the sound signals sent into the test object.

In yet another illustrative embodiment, a method for forming a sound inspection system is present. A flexible substrate is connected to an array of piezoelectric elements. An organic circuit system is formed on the flexible substrate with connections to the array of piezoelectric elements. The organic circuit system is configured to cause the array of piezoelectric elements to generate sound signals.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 6 is an illustration of a flexible ultrasound device in accordance with an illustrative embodiment;

FIG. 7 is an illustration of a portion of a flexible ultrasound device in accordance with an illustrative embodiment;

DETAILED DESCRIPTION

The illustrative embodiments recognize and take into account one or more different considerations. For example, the illustrative embodiments recognize and take into account that transducer arrays may be placed onto blankets that are flexible. For example, the blankets may be made of a flexible silicon or other suitable type of material. This placement of transducer arrays onto blankets may form a type of flexible ultrasound inspection system.

The illustrative embodiments, however, recognize and take into account that these types of flexible ultrasound inspection systems may be larger and more complex than desired. For instance, wires that are connected to all of the different transducers on the blanket may require more maintenance than desired.

Further, the illustrative embodiments recognize and take into account that the resolution of flexible ultrasound inspection systems may be lower than desired. The illustrative embodiments also recognize and take into account that the resolution of an ultrasound inspection system is limited to the size of the individual pixels. With ultrasound inspection systems, each transducer in a transducer array is a pixel in the ultrasound inspection system. The pixel size may be limited because of wires used to attach individual transducers to an analyzer system.

For example, an ultrasound transducer blanket having an array of pixels that are 128×128 may have 32,768 wires connected to the blanket. As a result, the transducers may be limited in size or spacing. In particular, the size of the transducers may be larger than desired because of the connections made using wires. Further, with the use of numerous wires, the amount of space between transducers may be greater than desired to accommodate the wires.

Thus, the illustrative embodiments provide a method and apparatus for inspecting an object. In these illustrative examples, the method and apparatus may use sound signals to inspect the object. In one illustrative embodiment, an apparatus comprises an array of piezoelectric elements, a flexible substrate, and an organic circuit system. The flexible substrate is formed on the array of piezoelectric elements and configured to substantially conform to a surface of a test object. The organic circuit system may be connected to the array of piezoelectric elements and is configured to cause the array of piezoelectric elements to send sound signals into the test object.

Figure 1:
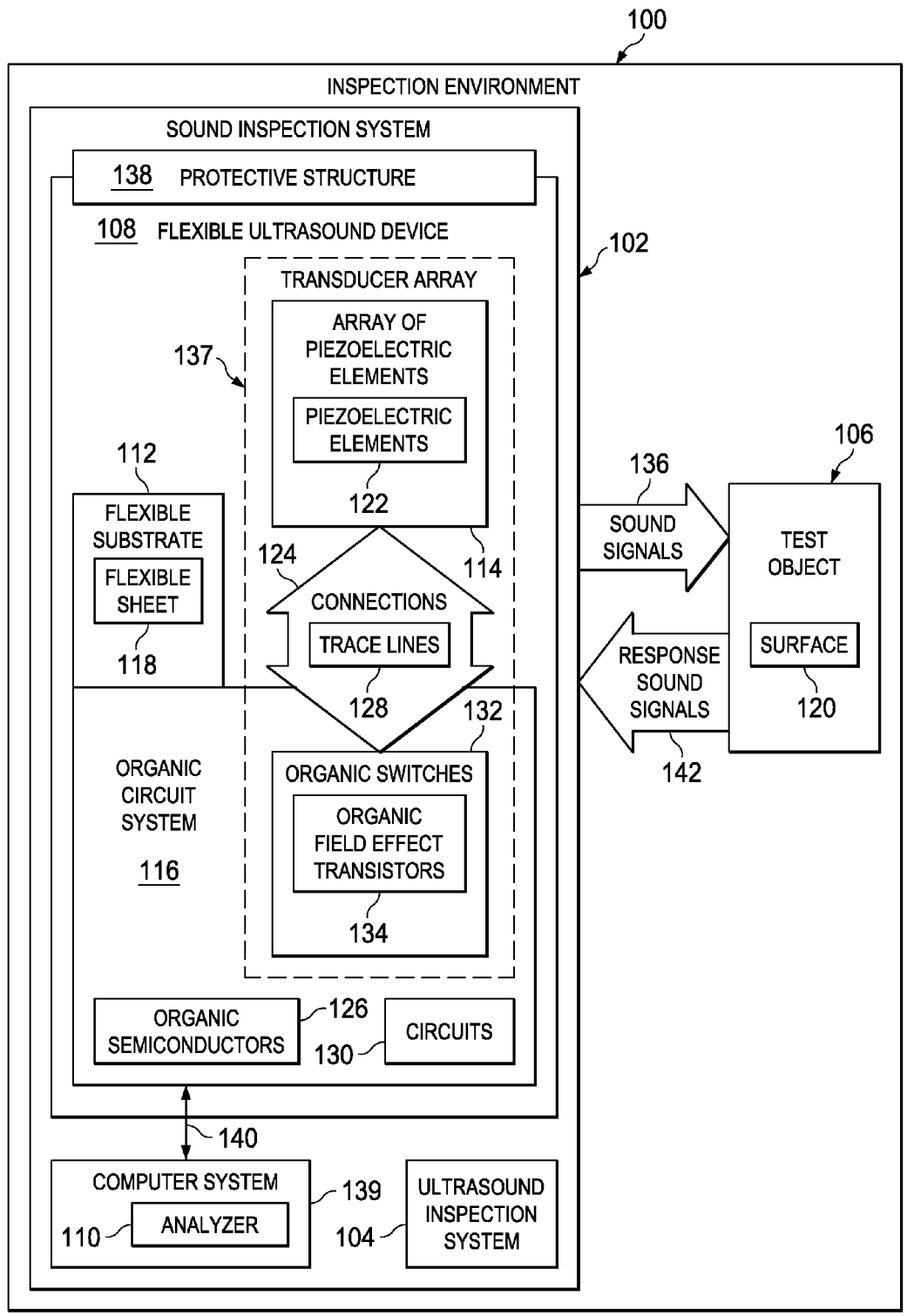
FIG. 1 is an illustration of a block diagram of an inspection environment in accordance with an illustrative embodiment.

Turning now to FIG. 1, an illustration of a block diagram of an inspection environment is depicted in accordance with an illustrative embodiment. As depicted, inspection environment 100 includes sound inspection system 102 which takes the form of ultrasound inspection system 104.

Sound inspection system 102 is used to inspect test object 106. Test object 106 may take various forms including fuselage barrel 506 in FIG. 5. Additionally, test object 106 may take other forms, such as, for example, without limitation, a horizontal stabilizer, an engine housing, a stringer, a composite panel, a wing, a flap, a pipe, a weld, and other suitable types of objects. In some illustrative examples, sound inspection system 102 also may be used to inspect test object 106 for corrosion.

In this illustrative example, ultrasound inspection system 104 includes flexible ultrasound device 108 and analyzer 110. Flexible ultrasound device 108 includes flexible substrate 112, array of piezoelectric elements 114, and organic circuit system 116. In these illustrative examples, flexible substrate 112 is formed on array of piezoelectric elements 114.

Additionally, organic circuit system 116 comprised of a number of circuits and is formed on at least one of flexible substrate 112 and array of piezoelectric elements 114. As used herein, a number of, when used with reference to items, means one or more items. For example, a number of circuits is one or more circuits.

In these illustrative examples, array of piezoelectric elements 114 may be comprised of a number of different types of materials. For example, without limitation, material used in array of piezoelectric elements 114 may be comprised of a number of materials selected from at least one of a crystal, a ceramic, quartz, topaz, gallium orthophosphate, barium titanate, bismuth ferrite, bismuth titanate, and polyvinylidene fluoride. Of course, other materials may be used for array of piezoelectric elements 114 depending on the particular implementation.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C. In other examples, "at least one of" may be, for example, without limitation, two of item A, one of item B, and ten of item C; four of item B and seven of item C; and other suitable combinations.

In these illustrative examples, flexible substrate 112 may be a number of different materials. For example, flexible substrate 112 may be selected from one of a flexible glass, a plastic, or other suitable types of materials.

As depicted, flexible substrate 112 may take the form of flexible sheet 118. Flexible sheet 118 may be selected such that flexible sheet 118 may substantially conform to surface 120 of test object 106. Array of piezoelectric elements 114 may be arranged in rows and columns or in some other format that corresponds to pixels suitable for generating image data. In other words, each piezoelectric element in piezoelectric elements 122 may generate data that is used as a pixel of an image.

Connections 124 between organic circuit system 116 and piezoelectric elements 122 may be formed during the manufacture of organic semiconductors 126. Connections 124 may be made using electrical connectors in these illustrative examples. For example, connections 124 may be made using trace lines 128 rather than wires.

As depicted, organic circuit system 116 and piezoelectric elements 122 in array of piezoelectric elements 114 may be integrated with each other during the manufacture of these components. In this manner, a higher resolution may be achieved than currently possible when using piezoelectric elements 122 with organic circuit system 116.

Flexible sheet 118 may be formed on piezoelectric elements 122. In other illustrative examples, piezoelectric elements 122 may be connected to flexible sheet 118 after flexible sheet 118 is formed. Flexible sheet 118 may be a single piece or multiple pieces that are associated with each other.

When one component is "associated" with another component, the association is a physical association in the depicted examples. For example, a first component may be considered to be associated with a second component by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

As depicted, piezoelectric elements 122 may be connected to flexible sheet 118 in a variety of different ways. For example, piezoelectric elements 122 may be connected to flexible sheet 118 using a flexible adhesive. In other illustrative examples, flexible sheet 118 may be grown on piezoelectric elements 122. Of course, piezoelectric elements 122 may be connected to flexible sheet 118 in any other manner, depending on the particular implementation.

In these illustrative examples, organic circuit system 116 comprises circuits 130 formed using organic semiconductors 126. In particular, circuits 130 are integrated circuits that may be formed using organic semiconductors 126. Organic semiconductors 126 may be any organic material with semiconductor properties.

In these illustrative examples, circuits 130 in organic circuit system 116 may include organic switches 132. Organic switches 132 may be, for example, organic field effect transistors 134.

Organic switches 132 are connected to piezoelectric elements 122 in array of piezoelectric elements 114. Organic switches 132 are configured to control the application of voltages to piezoelectric elements 122 to generate sound signals 136 in test object 106. As depicted, organic switches 132 and piezoelectric elements 122 form transducer array 137 in flexible ultrasound device 108.

Protective structure 138 is configured to protect organic circuit system 116. In these illustrative examples, protective structure 138 may be a flexible cover configured to cover organic circuit system 116. For example, protective structure 138 may protect organic circuit system 116 from environmental conditions that may be undesirable. These undesirable environmental conditions may include, for example, without limitation, dust, moisture, liquids, physical contact, and other undesirable conditions. In these illustrative examples, protective structure 138 may be an organic encapsulate, a polymer, an insulator, or another suitable type of material. These materials are selected as ones that may be flexible in a similar manner to flexible substrate 112 in these illustrative examples.

As depicted, organic circuit system 116 is in communication with computer system 139. This communication may be made through communications link 140. Communications link 140 may be a wired or wireless communication link depending on the particular implementation. Computer system 139 functions as analyzer 110. In particular, analyzer 110 may control the operation of flexible ultrasound device 108 in these illustrative examples.

As depicted, organic circuit system 116 is configured to cause array of piezoelectric elements 114 to send sound signals 136 into test object 106. For example, organic circuit system 116 may change voltages across piezoelectric elements 122 in array of piezoelectric elements 114 to generate sound signals 136 in test object 106.

In these illustrative examples, sound signals 136 generated by piezoelectric elements 122 may have various frequencies. Frequencies for sound signals 136 generated by piezoelectric elements 122 may be any frequency that travels through test object 106 and results in response sound signals 142 being generated. In these illustrative examples, sound signals 136 may take various forms such as ultrasonic sound signals. Ultrasonic sound signals may have a frequency from about 0.1 MHz to about 50 MHz depending on the particular implementation. Of course, other frequencies may be used depending on the particular implementation.

Response sound signals 142 are generated in test object 106 in response to sound signals 136 traveling through test object 106. Array of piezoelectric elements 114 may detect response sound signals 142 and generate signals that are received by organic circuit system 116 and protective structure 138.

In these illustrative examples, piezoelectric elements 122 may have a smaller size than is currently possible when using organic circuit system 116. For example, a piezoelectric element in piezoelectric elements 122 may have a size that is less than about 1 mm in length or diameter. This smaller size may occur through the formation of organic circuit system 116 using semiconductor processing techniques.

Although the illustrative examples of sound inspection system 102 and test object 106 are described with respect to an aircraft, an illustrative embodiment may be applied to other types of platforms other than those found in an aircraft. The platform may be, for example, a mobile platform, a stationary platform, a land-based structure, an aquatic-based structure, and a space-based structure.

More specifically, the platform may be a surface ship, a tank, a personnel carrier, a train, a spacecraft, a space station, a satellite, a submarine, an automobile, a power plant, a bridge, a dam, a house, a manufacturing facility, a building, and other suitable objects. Thus, sound inspection system 102 with flexible ultrasound device 108 may be used to inspect a variety of types of test objects.

Figure 2:
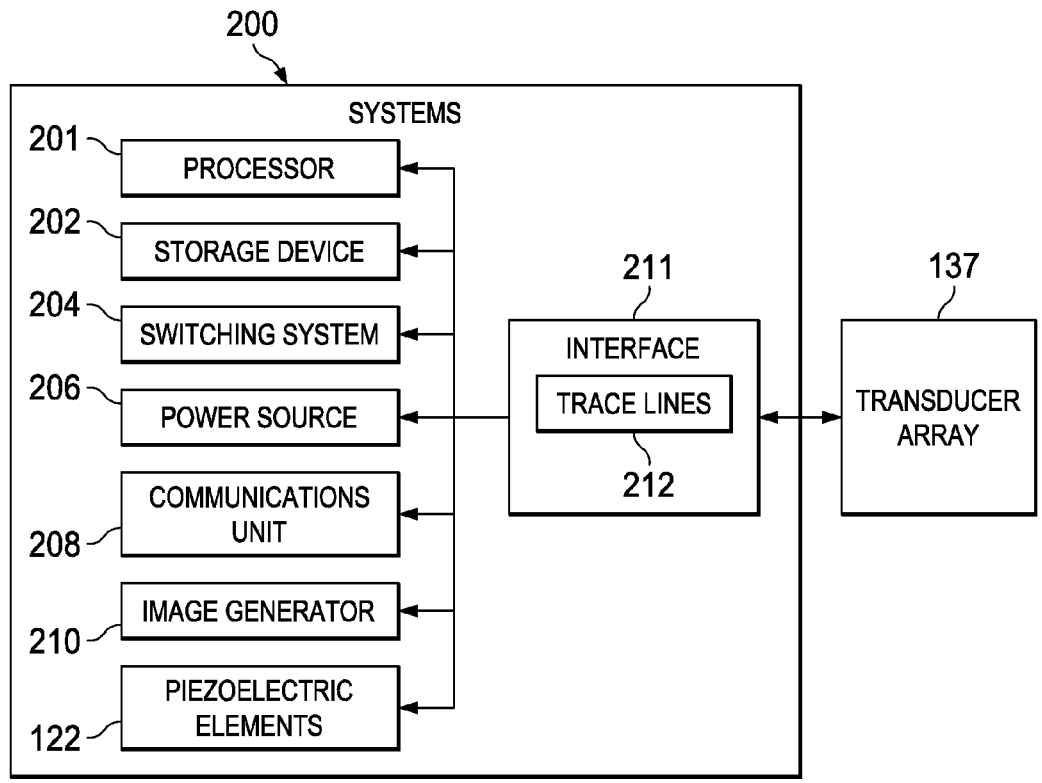
FIG. 2 is an illustration of a block diagram of examples of components in an organic circuit system in accordance with an illustrative embodiment.

Turning now to FIG. 2, an illustration of a block diagram of examples of components in an organic circuit system is depicted in accordance with an illustrative embodiment. In this illustrative example, circuits 130 in organic circuit system 116 may form various components in addition to transducer array 137 in FIG. 1.

For example, circuits 130 in organic circuit system 116 may form components in the form of systems 200. For example, circuits 130 in organic circuit system 116 may include at least one of processor 201, storage device 202, switching system 204, power source 206, communications unit 208, image generator 210, and interface 211. In other words, organic circuit system 116 may include one or more of these different systems and may include multiple systems of the same type depending on the particular implementation. All of the different systems in systems 200 are organic systems that are manufactured using organic semiconductors 126 from FIG. 1 in these illustrative examples.

Processor 201 is configured to process signals generated by piezoelectric elements 122 from detecting response sound signals 142 in FIG. 1. For example, without limitation, processor 201 may generate data from the signals, analyze the data, and perform other suitable types of processing. Further, processor 201 may also control the operation of other systems within systems 200.

Storage device 202 is configured to store information. This information may include data generated by processor 201 from signals sent by piezoelectric elements 122 in response to detecting response sound signals 142 in FIG. 1. Additionally, the information also may include commands, program code, and other suitable information.

As depicted, switching system 204 is configured to control which piezoelectric elements in piezoelectric elements 122 send sound signals 136. For example, switching system 204 may control piezoelectric elements 122 to cause groups of piezoelectric elements 122 in array of piezoelectric elements 114 to send sound signals 136 into test object 106 in a selected sequence. With the selected sequence, groups of piezoelectric elements 122 may send sound signals 136 one after another.

Power source 206 is configured to generate power in a form for use by other systems in systems 200. Power source 206 may, for example, convert an alternating current into a direct current or vice versa. In another illustrative example, power source 206 may include solar power cells. In yet another illustrative example, power source 206 may be configured to receive power using direct induction, resonant magnetic induction, electromagnetic radiation, or other suitable forms of power that may be transmitted wirelessly.

Communications unit 208 is configured to provide for an exchange of information between systems 200 in organic circuit system 116 and a remote device such as computer system 139 in FIG. 1. Communications unit 208 may take various forms. For example, communications unit 208 may be a network adapter, a wireless network adapter, a universal serial bus port, and other suitable types of devices that may exchange information.

As depicted, image generator 210 is configured to generate images using the data about response sound signals 142 generated by processor 201. In some illustrative examples, image generator 210 may generate data from the signals received from piezoelectric elements 122 caused by detecting response sound signals 142.

In these illustrative examples, images generated by image generator 210 may be stored in storage device 202. The images and other data stored in storage device 202 may be sent to a device using communications unit 208.

Interface 211 provides a connection between different systems in systems 200. This connection may be provided by trace lines 212 in interface 211.

For example, interface 211 may connect processor 201 and storage device 202 to each other. In this example, trace lines 212 in interface 211 may connect transducer array 137 to switching system 204 which in turn may be controlled by processor 201 through trace lines 212. In these illustrative examples, interface 211 may be comprised of trace lines 212. Further, trace lines 128 in FIG. 1 are a portion of trace lines 212 in these illustrative examples.

The illustration of inspection environment 100 and the different components in FIGS. 1 and 2 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although examples of systems 200 are shown in FIG. 2 for organic circuit system 116, organic circuit system 116 may include other types of systems or devices in addition to or in place of the ones illustrated. As depicted, organic circuit system 116 also may include filters in systems 200.

In some illustrative examples, only interface 211 and communications unit 208 may be present in systems 200. Communications unit 208 may receive signals from analyzer 110 in FIG. 1 that are sent to transducer array 137 through communications unit 208 and interface 211.

In another illustrative example, analyzer 110 may not be implemented in computer system 139 in FIG. 1. Instead, the different operations performed by analyzer 110 may be implemented in processor 201. In yet another illustrative example, inorganic circuits such as more traditional semiconductor circuits may be used along with organic circuit system 116.

Figure 3:
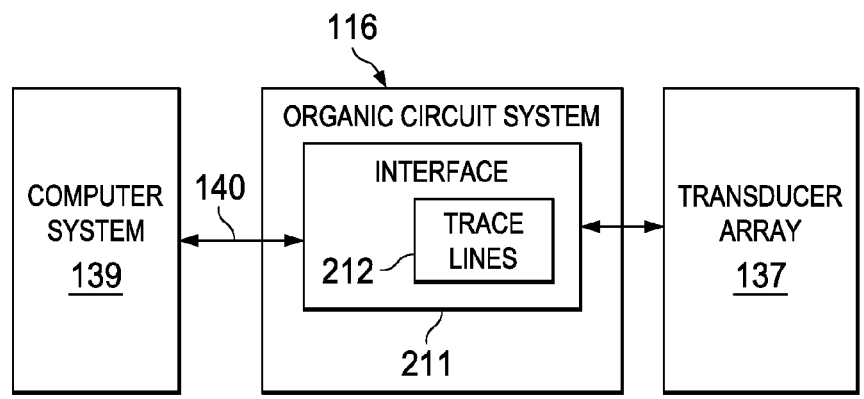
FIG. 3 is an illustration of a block diagram of systems in an organic circuit system in accordance with an illustrative embodiment.

Turning now to FIG. 3, an illustration of a block diagram of systems in an organic circuit system is depicted in accordance with an illustrative embodiment. In this illustrative example, an example of an implementation for organic circuit system 116 is shown.

One configuration for organic circuit system 116 includes interface 211 with trace lines 212 from systems 200 in FIG. 1. Interface 211 provides a connection to transducer array 137. Additionally, interface 211 also provides a connection to computer system 139 through communications link 140. In this illustrative example, communications link 140 takes the form of a ribbon cable.

Computer system 139 may send electrical signals to transducer array 137 through interface 211. These electrical signals may pass through interface 211 to transducer array 137. In turn, transducer array 137 sends sound signals 136 into test object 106 in FIG. 1. Additionally, when transducer array 137 detects response sound signals 142 in FIG. 1, transducer array 137 sends electrical signals through interface 211 back to computer system 139 for processing.

Figure 4:
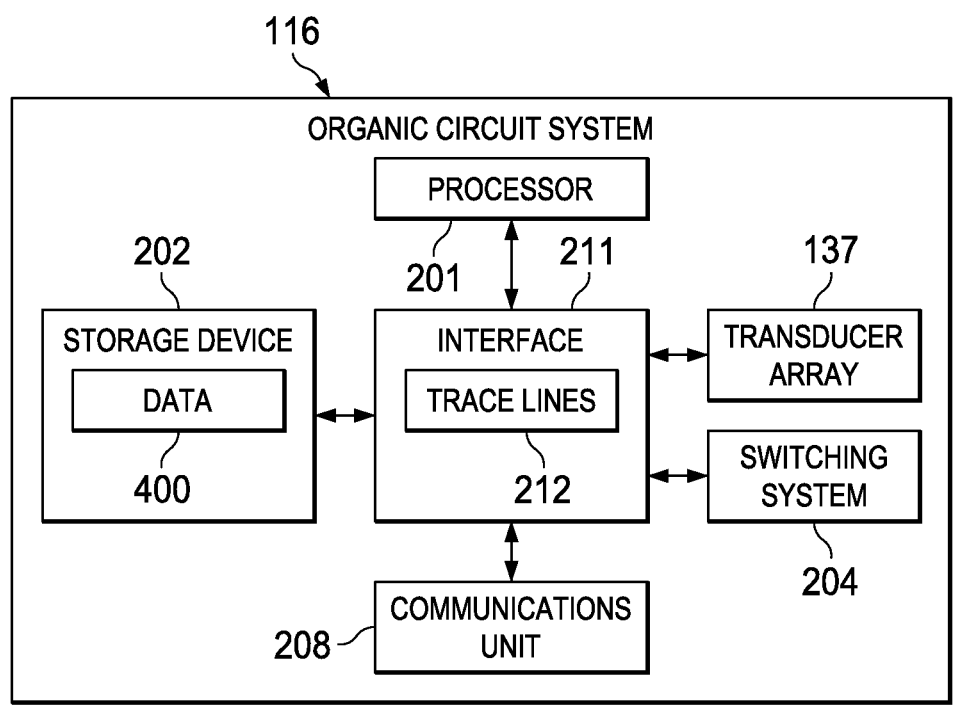
FIG. 4 is another illustration of a block diagram of systems in an organic circuit system in accordance with an illustrative embodiment.

Turning now to FIG. 4, another illustration of a block diagram of systems in an organic circuit system is depicted in accordance with an illustrative embodiment. In this illustrative example, an example of an implementation for organic circuit system 116 is shown.

In this illustrative example, another configuration for organic circuit system 116 is depicted. In this example, organic circuit system 116 is comprised of a number of circuits includes processor 201, storage device 202, switching system 204, communications unit 208, and interface 211.

As depicted, interface 211 with trace lines 212 provides connections between the different systems in organic circuit system 116. Additionally, interface 211 also provides a connection to transducer array 137.

In this illustrative example, processor 201 is configured to control the sending of sound signals 136 into test object 106 in FIG. 1 by transducer array 137. This control may be performed using switching system 204. Processor 201 may send electrical signals to switching system 204 such that switching system 204 causes piezoelectric elements 122 in transducer array 137 to send sound signals 136 in a selected manner.

For example, groups of piezoelectric elements 122 may send sound signals 136 into test object 106 in FIG. 1 in a selected sequence controlled by processor 201 through switching system 204. In other illustrative examples, all of piezoelectric elements 122 may send sound signals 136 into test object 106 in FIG. 1 at substantially the same time.

Further, response sound signals 142 in FIG. 1 detected by transducer array 137 are sent back to processor 201 for processing. Processor 201 may generate data 400 based on response sound signals 142 detected by transducer array 137 and save data 400 in storage device 202. In these illustrative examples, storage device 202 may be a buffer, a random access memory, or some other suitable type of storage device.

In these illustrative examples, processor 201 may send data 400 to a remote device such as computer system 139 in FIG. 1 over a wireless communications link through communications unit 208. Data 400 may be sent as data 400 is generated or may be sent periodically depending on the particular implementation.

The illustrations of configurations for organic circuit system 116 in FIGS. 3 and 4 are not meant to imply limitations to the manner in which organic circuit system 116 may be implemented. The examples of systems and configurations of the systems are only provided as examples of how organic circuit system 116 may be configured. Other configurations may be used depending on the particular implementation.

Figure 5:
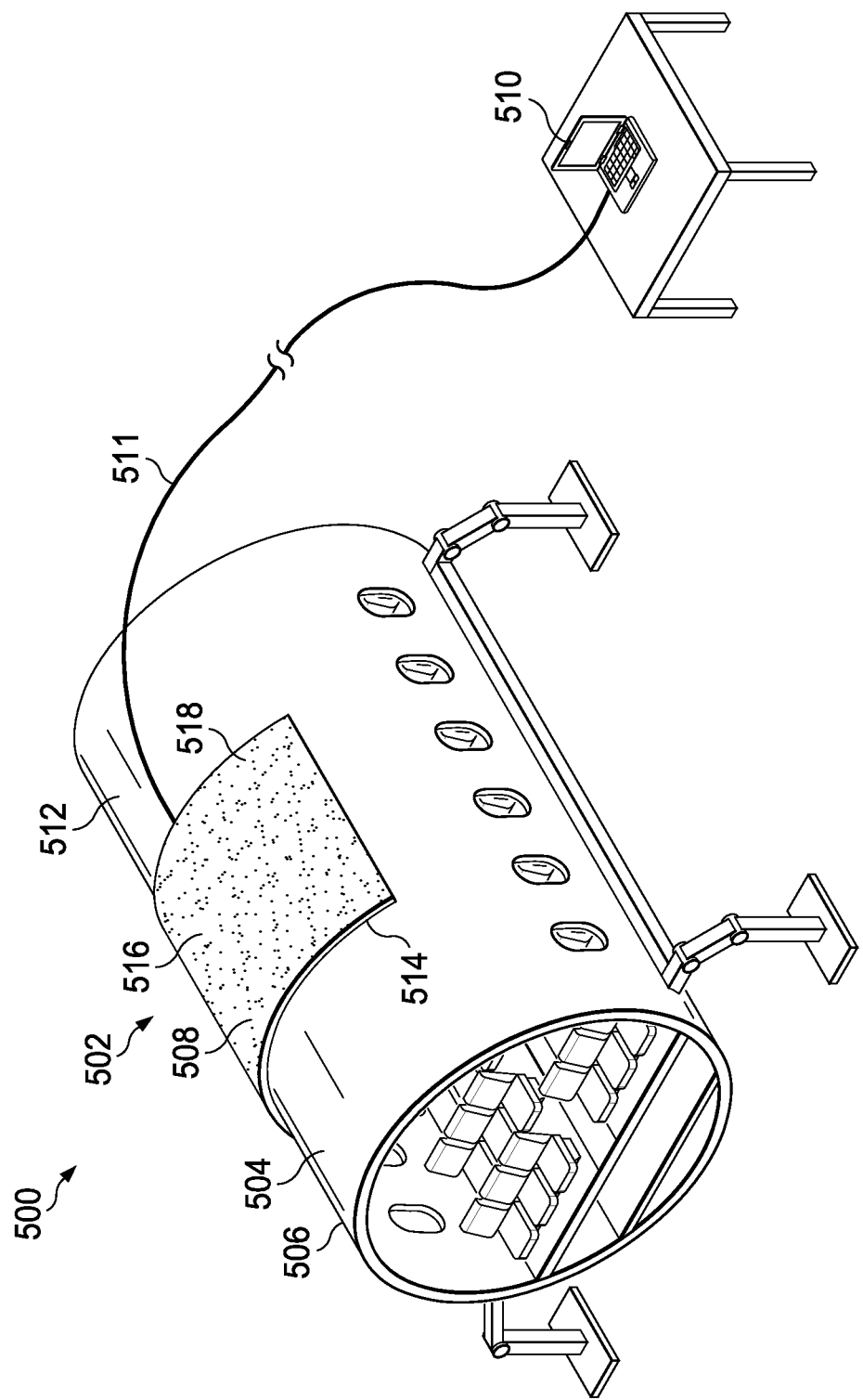
FIG. 5 is an illustration of an inspection environment in accordance with an illustrative embodiment.

With reference now to FIG. 5, an illustration of an inspection environment is depicted in accordance with an illustrative embodiment. Ultrasound inspection system 502 is a physical example of an implementation for ultrasound inspection system 104 shown in block form in FIG. 1.

As depicted, inspection environment 500 includes ultrasound inspection system 502. Ultrasound inspection system 502 is an example of a physical implementation for ultrasound inspection system 104 in FIG. 1. Ultrasound inspection system 502 may be used to inspect test object 504 in the form of fuselage barrel 506.

As illustrated, ultrasound inspection system 502 includes flexible ultrasound device 508 and computer 510. In this illustrative example, flexible ultrasound device 508 is an example of an implementation for flexible ultrasound device 108 in FIG. 1. Flexible ultrasound device 508 is in communication with computer 510 through cable 511. Flexible ultrasound device 508 is configured to generate sound signals in fuselage barrel 506. In these illustrative examples, the sound signals are ultrasound signals.

Further, flexible ultrasound device 508 is configured to detect response sound signals generated in response to the sound signals sent into fuselage barrel 506. Flexible ultrasound device 508 is configured to generate data in response to detecting the response sound signals. This data may take the form of electrical signals indicating information such as an amplitude, a time, and other information about the response sound signals detected by flexible ultrasound device 508.

In this illustrative example, flexible ultrasound device 508 is configured to substantially conform to surface 512 of fuselage barrel 506. In particular, flexible ultrasound device 508 is comprised of transducer system 514, flexible sheet 516, and organic circuit system 518.

Turning now to FIG. 6, an illustration of a flexible ultrasound device is depicted in accordance with an illustrative embodiment. In this illustrative example, a perspective view of flexible ultrasound device 108 is shown.

As depicted, flexible sheet 516 in flexible ultrasound device 508 has first side 600 and second side 602. In this illustrative example, piezoelectric elements 604 can be seen in transducer system 514 on second side 602.

In these illustrative examples, organic circuit system 518 may be located on at least one of first side 600 and second side 602 of flexible sheet 516. In these illustrative examples, flexible sheet 516 may form a substrate for organic circuit system 518.

In other illustrative examples, all of organic circuit system 518 including the substrate may be formed on flexible sheet 516 depending on the particular implementation. Further, a portion of organic circuit system 518 also may be formed on piezoelectric elements 604. A description of section 606 of flexible ultrasound device 508 is described in FIG. 7 below.

With reference now to FIG. 7, an illustration of a portion of a flexible ultrasound device is depicted in accordance with an illustrative embodiment. In this illustrative example, a more detailed illustration of section 606 of flexible ultrasound device 508 is shown.

In section 606, piezoelectric element 700, piezoelectric element 702, and piezoelectric element 704 in piezoelectric elements 604 are depicted on second side 602. Additionally, circuits 708 are seen on piezoelectric element 700 on second side 602 of flexible sheet 516.

Further, circuits 710 are also seen on first side 600 of flexible sheet 516 through an exposed view of a portion of protective structure 712. In this illustrative example, protective structure 712 is configured to protect circuits 710 in organic circuit system 518 on first side 600.

In these illustrative examples, protective structure 712 may encapsulate circuits 710 and piezoelectric element 700, or both. For example, protective structure 712 may be a flexible silicon cover that behaves as a coupler between a test object and piezoelectric element 700.

As an example, protective structure 712 may behave as a coupler between surface 512 of fuselage barrel 506 in FIG. 5 and piezoelectric element 700. Of course, protective structure 712 may be comprised of another type of material other than silicon and may not encapsulate substantially all of circuits 710 and/or piezoelectric element 700, depending on the particular implementation. A more detailed illustration of section 714 is described in FIG. 8 below.

Figure 8:
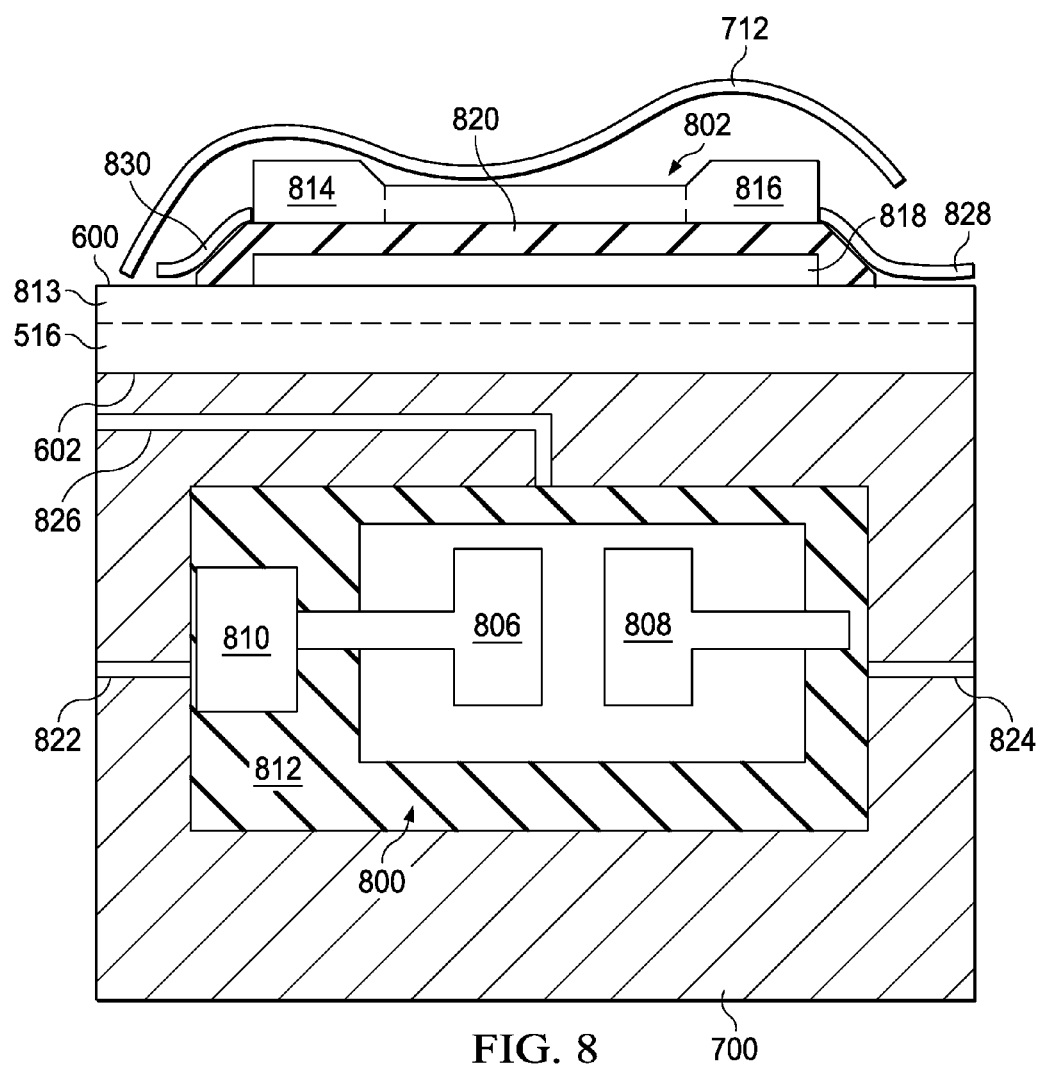
FIG. 8 is an illustration of a more detailed view of a portion of a flexible ultrasound device in accordance with an illustrative embodiment.

With reference now to FIG. 8, an illustration of a more detailed view of a portion of a flexible ultrasound device is depicted in accordance with an illustrative embodiment. In this illustrative example, a side view of section 714 in FIG. 7 is shown.

In this view, circuits 708 in FIG. 7 include organic transistor 800 and circuits 710 in FIG. 7 include organic transistor 802. As depicted, organic transistor 800 is formed on piezoelectric element 700. Organic transistor 800 may be implemented using any suitable architecture for semiconductor transistors. For example, organic transistor 800 may be a thin-film transistor formed using organic materials. In this view, organic transistor 800 has source 806, drain 808, gate 810, and polymer dielectric 812.

Substrate 813 is formed on first side 600 of flexible sheet 516. Organic transistor 802 is formed on substrate 813. In other illustrative examples, flexible sheet 516 may be a substrate for organic transistor 802. In this example, organic transistor 802 also may be implemented using any desired architecture used for semiconductor transistors. As depicted, organic transistor 802 has source 814, drain 816, gate 818, and polymer dielectric 820.

In this illustrative example, trace lines 822, 824, 826, 828, and 830 are also illustrated in these examples. In particular, trace line 822 is connected to source 806. Trace line 824 is connected to drain 808, and trace line 826 is connected to gate 810 in organic transistor 802. Trace line 828 is connected to drain 816 and trace line 830 is connected to source 814. A connection of gate 818 to a trace line is not shown in this view.

With the use of a deposited trace line, the size of piezoelectric element 700 may be reduced as compared to the use of bonding wires to circuits. Thus, reducing the size of piezoelectric element 700 may allow for an increase in the resolution in images that may be generated from a transducer array.

The illustration of flexible ultrasound device 508 and the different components in FIGS. 5-8 are not meant to imply limitations to the manner in which other flexible ultrasound devices may be implemented. For example, in other implementations, organic circuits may only be present on one side of flexible sheet 516. In other illustrative examples, non-organic circuits also may be included with the organic circuits.

In another illustrative example, circuits within organic circuit system 518 in FIG. 5 may be formed in other locations in addition to or in place of first side 600 and second side 602 of flexible sheet 516. For example, circuits for organic circuit system 518 in FIG. 5 may be formed within flexible sheet 516 during the manufacturing of flexible sheet 516.

Figure 9:
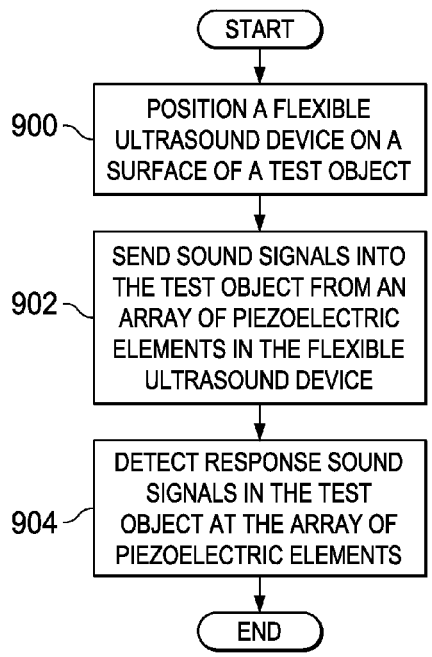
FIG. 9 is an illustration of a flowchart of a process for inspecting a test object in accordance with an illustrative embodiment.

Turning now to FIG. 9, an illustration of a flowchart of a process for inspecting a test object is depicted in accordance with an illustrative embodiment. The process illustrated in FIG. 9 may be implemented in inspection environment 100 in FIG. 1. Further, this process may be implemented using sound inspection system 102.

The process begins by positioning a flexible ultrasound device on a surface of a test object (operation 900). The flexible ultrasound device is configured to substantially conform to the surface of the test object. The process then sends sound signals into the test object from an array of piezoelectric elements in the flexible ultrasound device (operation 902).

The process detects response sound signals in the test object at the array of piezoelectric elements (operation 904), with the process terminating thereafter.

The response sound signals detected by the array of piezoelectric elements may be analyzed. Further, images may be generated from the response sound signals detected by the array of piezoelectric elements.

Figure 10:
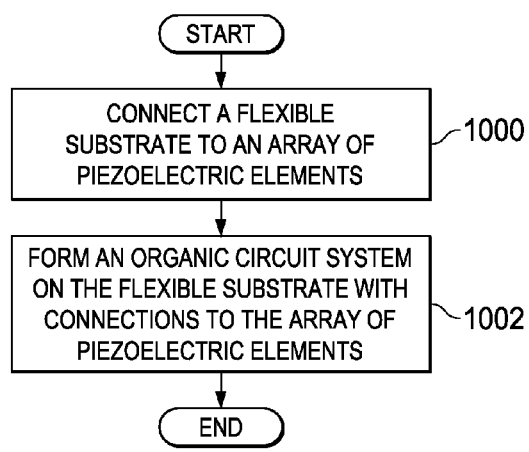
FIG. 10 is an illustration of a flowchart of a process for forming an ultrasound inspection system in accordance with an illustrative embodiment.

Turning now to FIG. 10, an illustration of a flowchart of a process for forming an ultrasound inspection system is depicted in accordance with an illustrative embodiment. The process illustrated in FIG. 10 may be used to manufacture sound inspection system 102. In particular, the process may be used to manufacture flexible ultrasound device 108 in FIG. 1.

The process begins by connecting a flexible substrate to an array of piezoelectric elements (operation 1000). The connection made in operation 1000 may be formed in a number of different ways. For example, the flexible substrate may be formed on piezoelectric elements in the array of piezoelectric elements. In another example, the flexible substrate may be bonded to the piezoelectric elements.

The process then forms an organic circuit system on the flexible substrate with connections to the array of piezoelectric elements (operation 1002), with the process terminating thereafter. Operation 1002 may be performed using any currently known techniques for fabricating organic circuits.

For example, organic circuits may be formed through various currently used organic semiconductor fabrication processes. For example, the semiconductor devices in the organic circuits may be printed on a substrate, such as a flexible sheet using inkjet printing technologies. This type of fabrication may be performed at room temperature. Of course, any other suitable process for fabricating organic semiconductors may be used.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 11:
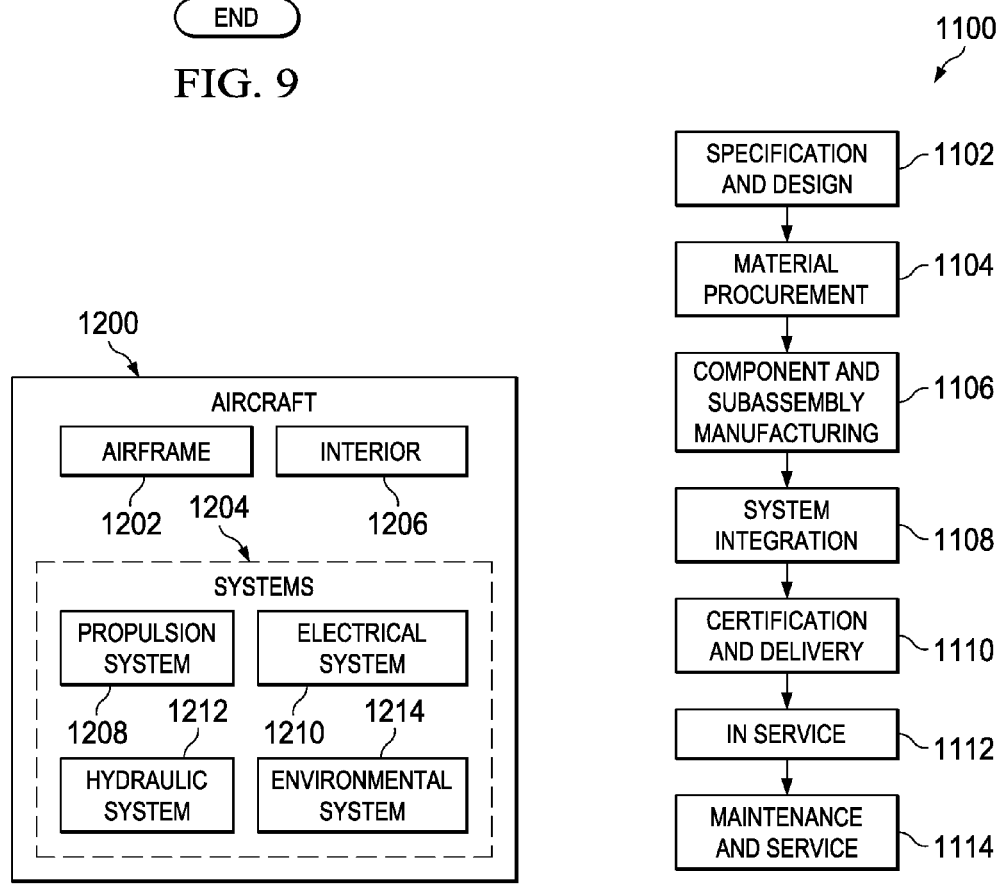
FIG. 11 is an illustration of an aircraft manufacturing and service method in accordance with an illustrative embodiment.
Figure 12:
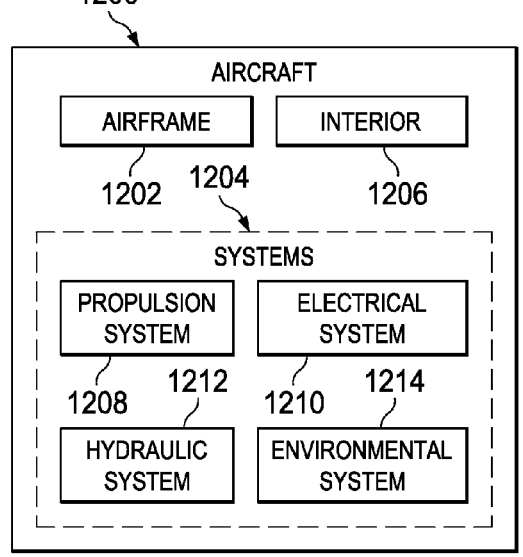
FIG. 12 is an illustration of an aircraft in which an illustrative embodiment may be implemented.

Illustrative embodiments of the disclosure may be described in the context of aircraft manufacturing and service method 1100 as shown in FIG. 11 and aircraft 1200 as shown in FIG. 12. Turning first to FIG. 11, an illustration of an aircraft manufacturing and service method is depicted in accordance with an illustrative embodiment. During pre-production, aircraft manufacturing and service method 1100 may include specification and design 1102 of aircraft 1200 in FIG. 12 and material procurement 1104.

During production, component and subassembly manufacturing 1106 and system integration 1108 of aircraft 1200 in FIG. 12 takes place. Thereafter, aircraft 1200 in FIG. 12 may go through certification and delivery 1110 in order to be placed in service 1112. While in service 1112 by a customer, aircraft 1200 in FIG. 12 is scheduled for routine maintenance and service 1114, which may include modification, reconfiguration, refurbishment, and other types of maintenance or service.

Each of the processes of aircraft manufacturing and service method 1100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 12, an illustration of an aircraft is depicted in which an illustrative embodiment may be implemented. In this example, aircraft 1200 is produced by aircraft manufacturing and service method 1100 in FIG. 11 and may include airframe 1202 with plurality of systems 1204 and interior 1206. Examples of systems 1204 include one or more of propulsion system 1208, electrical system 1210, hydraulic system 1212, and environmental system 1214. Any number of other systems may be included.

Although an aerospace example is shown, different illustrative embodiments may be applied to other industries, such as the automotive industry.

Apparatuses and methods embodied herein may be employed during at least one of the stages of aircraft manufacturing and service method 1100 in FIG. 11. For example, sound inspection system 102 may be used to perform inspections of components or subassemblies manufactured during components and subassembly manufacturing 1106. Additionally, inspections may be performed using sound inspection system 102 while aircraft 1200 is in service 1112 or during maintenance and service 1114. The use of a number of the different illustrative embodiments may substantially expedite the assembly of and/or reduce the cost of aircraft 1200.

Thus, the illustrative embodiments may be used to manufacture sound inspection systems, such as ultrasound inspection systems, that have a greater resolution than currently available ultrasound inspections systems. Further, sound inspection systems in the illustrative examples may include flexible ultrasound devices that may substantially conform to the surface of a test object. In particular, the flexible ultrasound devices in the illustrative examples may provide an ability to conform to surfaces that may have curves, angles, or other features that may be more extreme or complex as compared to currently used ultrasound inspection systems.

Also, the complexity and number of wires connected to piezoelectric elements may be reduced through the use of organic circuits. In particular, trace lines may be used in an organic circuit system to provide desired connections. As a result, external wiring hookups may be reduced or eliminated in the illustrative examples.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
   an array of piezoelectric elements;
   a flexible substrate connected to the array of piezoelectric elements and configured to substantially conform to a surface of a test object; and
   an organic circuit system partially formed on the flexible substrate and at least a portion of the organic circuit system being directly formed on the array of piezoelectric elements, the organic circuit system being connected to the array of piezoelectric elements, wherein the organic circuit system is configured to cause the array of piezoelectric elements to send sound signals into the test object wherein the at least the portion of the organic circuit system comprises:
   organic field effect transistors formed directly on the array of piezoelectric elements such that the field effect transistors are integrated with the piezoelectric elements; and
   trace lines formed during manufacture of the organic circuit system, the trace lines connecting the organic field effect transistors to the array of piezoelectric elements.

2. The apparatus of claim 1, wherein the organic circuit system is further configured to receive signals generated by the array of piezoelectric elements from detecting response sound signals in the test object.

3. The apparatus of claim 1, wherein the organic circuit system is configured to cause groups of piezoelectric elements in the array of piezoelectric elements to send the sound signals into the test object in a selected sequence.

4. The apparatus of claim 1, wherein the organic field effect transistors are configured to change voltages across piezoelectric elements in the array of piezoelectric elements in a manner that generates the sound signals in the test object.

5. The apparatus of claim 4, wherein the organic field effect transistors and the array of piezoelectric elements form a transducer array.

6. The apparatus of claim 1, wherein the organic circuit system comprises at least one of a number of circuits selected from at least one of a processor, a storage device, a switching system, a power source, a communications unit, and an image generator.

7. The apparatus of claim 1 further comprising:
   a flexible cover configured to cover the organic circuit system.

8. The apparatus of claim 1, wherein the flexible substrate is comprised of a material selected from one of a flexible glass and a plastic.

9. The apparatus of claim 1, wherein the array of piezoelectric elements is comprised of a number of materials selected from at least one of a crystal, a ceramic, quartz, topaz, gallium orthophosphate, barium titanate, bismuth ferrite, bismuth titanate, and polyvinylidene fluoride.

10. A method for inspecting a test object, the method comprising:
    positioning a flexible ultrasound device on a surface of the test object wherein the flexible ultrasound device includes an array of piezoelectric elements; a flexible substrate connected to the array of piezoelectric elements and configured to substantially conform to the surface of the test object; and an organic circuit system partially formed on the flexible substrate and at least a portion of the organic circuit system being directly formed on the array of piezoelectric elements, the organic circuit system being connected to the array of piezoelectric elements;
    sending sound signals into the test object from the array of piezoelectric elements; and
    detecting response sound signals in the test object at the array of piezoelectric elements, wherein the response sound signals are generated in response to the sound signals sent into the test object;
    wherein the at least the portion of the organic circuit system comprises organic field effect transistors formed directly on the array of piezoelectric elements such that the field effect transistors are integrated with the piezoelectric elements; and
    trace lines formed during manufacture of the organic circuit system, the trace lines connecting the organic field effect transistors to the array of piezoelectric elements.

11. The method of claim 10 further comprising:
generating an image of the test object using the response sound signals detected at the array of piezoelectric elements.

12. The method of claim 10, wherein sending the sound signals into the test object from the array of piezoelectric elements comprises:
sending groups of the sound signals into the test object from groups of piezoelectric elements in the array of piezoelectric elements in a selected sequence.

13. The method of claim 10 further comprising:
sending data as the data is generated from detecting the response sound signals at the array of piezoelectric elements.

14. The method of claim 10 further comprising:
sending data when all of the data is generated from one of the response sound signals at the array of piezoelectric elements.

15. The method of claim 10, wherein the organic circuit system comprises a number of circuits selected from at least one of a processor, a storage device, a switching system, a power source, a communications unit, and an image generator.

16. A method for forming a sound inspection system, the method comprising:
connecting a flexible substrate to an array of piezoelectric elements; and
partially forming an organic circuit system on the flexible substrate, forming at least a portion of the organic circuit system directly on the array of piezoelectric elements and connecting the organic circuit system to the array of piezoelectric elements, wherein the organic circuit system is configured to cause the array of piezoelectric elements to generate sound signals;
wherein the at least the portion of the organic circuit system comprises organic field effect transistors formed directly on the array of piezoelectric elements such that the field effect transistors are integrated with the piezoelectric elements; and
trace lines formed during manufacture of the organic circuit system, the trace lines connecting the organic field effect transistors to the array of piezoelectric elements.

17. The method of claim 16, wherein connecting the flexible substrate to the array of piezoelectric elements comprises:
forming the flexible substrate on piezoelectric elements in the array of piezoelectric elements.

18. The method of claim 16, wherein connecting the flexible substrate to the array of piezoelectric elements comprises:
bonding the flexible substrate to piezoelectric elements in the array of piezoelectric elements.

* * * * *